(12) United States Patent
King et al.

(10) Patent No.: US 11,931,529 B2
(45) Date of Patent: Mar. 19, 2024

(54) STEERABLE CATHETER

(71) Applicant: Aran Biomedical Teoranta, Galway (IE)

(72) Inventors: Dean King, Galway (IE); Stephen Duffy, Galway (IE); Paul Flaherty, Galway (IE)

(73) Assignee: Aran Biomedical Teoranta, Galway (IE)

( * ) Notice: Subject to any disclaimer, the term of this patent is extended or adjusted under 35 U.S.C. 154(b) by 664 days.

(21) Appl. No.: 16/981,888

(22) PCT Filed: Mar. 25, 2019

(86) PCT No.: PCT/EP2019/057414
§ 371 (c)(1),
(2) Date: Sep. 17, 2020

(87) PCT Pub. No.: WO2019/180268
PCT Pub. Date: Sep. 26, 2019

(65) Prior Publication Data
US 2021/0001089 A1 Jan. 7, 2021

(30) Foreign Application Priority Data

Mar. 23, 2018 (IE) .................................. S2018/0064

(51) Int. Cl.
*A61M 25/01* (2006.01)
*A61M 25/00* (2006.01)
(52) U.S. Cl.
CPC .... *A61M 25/0147* (2013.01); *A61M 25/0012* (2013.01); *A61M 25/0026* (2013.01); *A61M 25/0136* (2013.01); *A61M 2025/015* (2013.01)

(58) Field of Classification Search
CPC .......... A61M 25/0147; A61M 25/0012; A61M 25/0026; A61M 25/0136; A61M 2025/015
See application file for complete search history.

(56) References Cited

U.S. PATENT DOCUMENTS

| | | | |
|---|---|---|---|
| 2004/0122360 A1 | 6/2004 | Waldhauser | |
| 2008/0312506 A1* | 12/2008 | Spivey | A61M 25/0138 600/149 |
| 2011/0106101 A1 | 5/2011 | Tortonese | |
| 2016/0114133 A1* | 4/2016 | Thorstenson | A61M 25/0662 604/95.04 |
| 2017/0258614 A1 | 9/2017 | Griffin | |
| 2018/0001058 A1* | 1/2018 | Schlesinger | A61B 34/74 |
| 2021/0001088 A1* | 1/2021 | Brannick | A61M 25/0662 |

FOREIGN PATENT DOCUMENTS

| | | |
|---|---|---|
| WO | 2004096015 A2 | 11/2004 |
| WO | 2016114981 A1 | 7/2016 |

OTHER PUBLICATIONS

Jun. 27, 2019 International Search Report and Written Opinion in corresponding PCT Application No. PCT/ EP2019/057414.

\* cited by examiner

*Primary Examiner* — Laura A Bouchelle
*Assistant Examiner* — John A Doubrava
(74) *Attorney, Agent, or Firm* — Michael F. Scalise

(57) ABSTRACT

The present invention provides a steerable medical or surgical device, in particular a steerable catheter having one or more actuators which may be integrated into a catheter without the need for welding the actuator to the catheter, the device comprising a main shaft having a proximal end and a distal end, and at least one braided actuator coupled to the main shaft at or adjacent the distal end.

21 Claims, 3 Drawing Sheets

STEERABLE CATHETER

This patent application is a 35 U.S.C 371 national stage application of International Patent Application No. PCT/EP2019/057414, filed on Mar. 25, 2019, which claims priority to Irish Patent Application No. S2018/0064, filed on Mar. 23, 2018. All of these disclosures are hereby expressly incorporated by reference as part of the present disclosure as if fully set forth herein.

FIELD OF THE INVENTION

This invention relates to a steerable medical or surgical device, in particular a steerable catheter having one or more actuators which may be integrated into a catheter without the need for welding the actuator to the catheter.

BACKGROUND OF THE INVENTION

In the field of steerable medical devices, for example steerable catheters, conventional metal wire actuators are typically welded to a metal 'pull ring' situated at the distal end of the catheter. The actuators are typically placed inside lumens that run along the vertical axis of the catheter. By pulling on any one of the actuators the distal tip of the catheter is deflected towards the side to which that actuator is secured to the pull ring, facilitating the remote steering of the tip, with a suitable mechanism generally being provided at the handle of the catheter in order to apply tension to the actuators such as to deflect the tip.

The need to weld each of the actuators to a metal pull ring significantly limits the choice of materials that can be considered to produce the actuators, in particular limiting the actuators to being formed from metals or metal alloys.

In addition the use of metal actuators also prevents such steerable medical devices being located within a patient when that patient is to be placed within or scanned by additional medical equipment not suitable for use with metal, for example a magnetic resonance imaging (MRI) device or similar equipment.

It is therefore an object of the present invention to address the above mentioned shortcomings of prior art steerable medical devices.

SUMMARY OF THE INVENTION

According to a first aspect of the present invention there is provided a steerable medical device comprising a main shaft having a proximal end and a distal end; and at least one braided actuator coupled to the main shaft at or adjacent the distal end.

Preferably, the medical device comprises a braided sheath at least partially surrounding the main shaft and with which the at least one braided actuator is integrated.

Preferably, the at least one braided actuator is interwoven with the braided sheath.

Preferably, the medical device comprises a retaining ring secured at or adjacent the distal end and to which the at least one actuator is coupled.

Preferably, the retaining ring comprises at least anchor point to which the at least one actuator is secured.

Preferably, the at least one anchor point comprises an aperture through which the at least one actuator is passed.

Preferably, the anchor point comprises at least one abutment to which the at least one actuator is secured.

Preferably, the at least one actuator comprises an integrated distal fastener by which the actuator is coupled to the main shaft.

Preferably, the integrated distal fastener comprises a closed loop formed at an end of the actuator.

Preferably, the at least one actuator comprises an integrated proximal fastener.

Preferably, the at least one actuator comprises an outward leg extending towards the distal end and a return leg extending from the distal end towards the proximal end.

Preferably, the medical device comprises a liner disposed between the main shaft and the braided sheath.

Preferably, the main braid is formed from non metallic material.

Preferably, the main braid is formed from polymeric material.

Preferably, the medical device comprises an outer sleeve encapsulating at least a portion of the braided sheath.

Preferably, the outer sleeve is at least partially affixed to the braided sheath.

Preferably, the outer sleeve is at least partially reflowed over the braided sheath.

Preferably, the main shaft comprises one or more lumens.

Preferably, one or more of the lumens define a return path from the distal end for the at least one actuator.

Preferably, the medical device comprises at least a pair of diametrically disposed actuators.

Preferably, the medical device comprises an array of actuators circumferentially equally spaced around the main shaft.

Preferably, the medical device comprises a catheter.

As used herein, the term "proximal" or "proximal end" is a relative term intended to refer to a location at, adjacent, towards or closer than another location or end of a medical device such as a catheter, relative to a reference point or location, such as an operator of the catheter.

As used herein, the term "distal" or distal end" is a relative term intended to refer to a location away or further than another location or end of a medical device, in particular a catheter, and most particularly is intended to mean relatively further from an operator of the catheter.

BRIEF DESCRIPTION OF THE DRAWINGS

The present invention will now be described with reference to the accompanying drawings, in which.

DETAILED DESCRIPTION OF THE DRAWINGS

Figure 1:
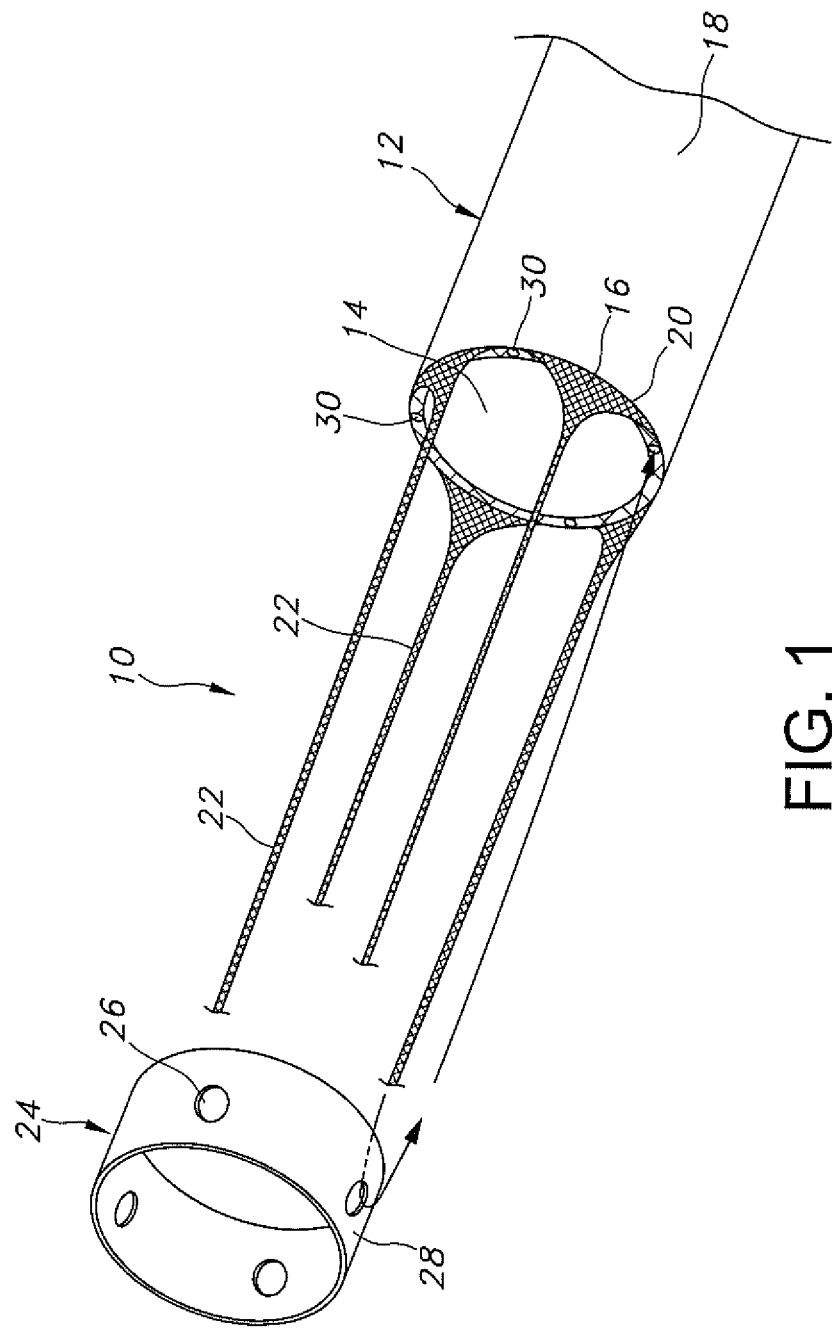
FIG. 1 illustrates a perspective view of a first embodiment of a steerable medical device according to the present invention.

Referring now to FIG. 1 of the accompanying drawings, there is illustrated a steerable medical device according to a first embodiment of the present invention, generally indicated as 10, and which has particular application as a steerable catheter 10 for use in various surgical/medical applications as are well known in the art. Steerable catheters and other medical devices are particularly useful in navigating winding or tortuous body lumens, for example the vascular system of a patient, in order to access a remote site for the purposes of performing some form of medical procedure or examination, such as stent delivery or the like. Generally speaking the distal or leading tip of the catheter may be deflected in a number of different directions in order to navigate the body lumen in question and thus avoid trauma to the patient, while also reducing operating times and consequently reducing recovery times and costs of the surgical/medical procedures in question.

The steerable catheter 10 of this first embodiment and the further embodiments described hereinafter, differ from known steerable catheters in the materials used for and the construction of the components used to effect steering of the catheter 10, as will be described in detail hereinafter, enabling use of the catheter 10 is situations that would otherwise not be permissible.

The catheter 10 comprises a hollow main shaft 12 which defines a main lumen 14 extending longitudinally through the catheter 10 and through which, in use, various surgical and/or medical operations may be performed as is well known in the art. The main shaft 12 may be of any suitable size and shape, for example 4 French, 6 French, 20 French etc. and may be formed from any suitable material or combination of materials, in order to suit the particular surgical or medical application. It will be understood by persons skilled in the art that the catheter 10 may incorporate any number of additional features and/or components, such as additional lumens (not shown), external balloons for deploying related devices such as implants or stents (not shown), occluding vascular pathways, or any other functions.

In the embodiment illustrated, the catheter 10 comprises a braided sheath 16 which surrounds the exterior surface of the main shaft 12 over at least a portion of the length of the shaft 12. The configuration of the braided sheath 16 may be varied as required, and in the embodiment illustrated is a forty-eight-end braid with all of the individual braids preferably being formed from a polymeric material although it should also be understood that one or more of the braids, and potentially all of the braids, may be formed from a metallic material such as nitinol or stainless steel wire or the like.

The braided sheath 16 may be secured to the exterior of the main shaft 12 by reflowing a polymer outer jacket (not shown) over at least a portion of the length of the main shaft 12, and preferably the entire length of the main shaft 12 about which the braided sheath 16 is located.

The main shaft 12 includes a proximal end 18 and an opposed distal end 20 which in use is the end that is desired to be steered and thus in use defines the working tip of the catheter 10. At or adjacent to the distal end 20, the braided sheath 16 splits into one or more braided actuators 22, and in the embodiment illustrated is split into four such braided actuators 22, which are equally spaced from one another about the circumference of the main shaft 12 and are therefore separated from one another through 90°.

Each of the braided actuators 22 extends longitudinally beyond the distal end 20 before being coupled to an annular retaining ring or pull ring 24, which in use will effectively define the working tip of the catheter 10. While the braided actuators 22 may be both coupled to and terminate at the pull ring 24, in the embodiment illustrated each braided actuator 22 is passed through an anchor point in the form of an opening 26 in a side wall 28 of the pull ring 24, before reversing in direction and passing into a respective auxiliary lumen 30 in the main shaft 12. Thus, in the embodiment illustrated the main shaft 12 defines four of the auxiliary lumens 30 equally spaced from one another around the circumference of the main shaft 12.

Each of the braided actuators 22 then extends through the respective auxiliary lumen 30 along the full length of the main shaft 12 to terminate at a handle (not shown) of the catheter 10 where each of the braided actuators 22 is suitably secured to a tensioning mechanism (not shown) which is operable to apply tension to the individual actuators 22. This tension is therefore transmitted to the pull ring 24, and in particular to one or more points on the pull ring 24 corresponding to the openings 26, which will therefore result in a deflection or deformation of the distal end 20 of the catheter 10 towards that side of the pull ring 24 in which the respective opening 28 is located, allowing the tip of the catheter 10 to be remotely steered or directed as required.

Figure 2:
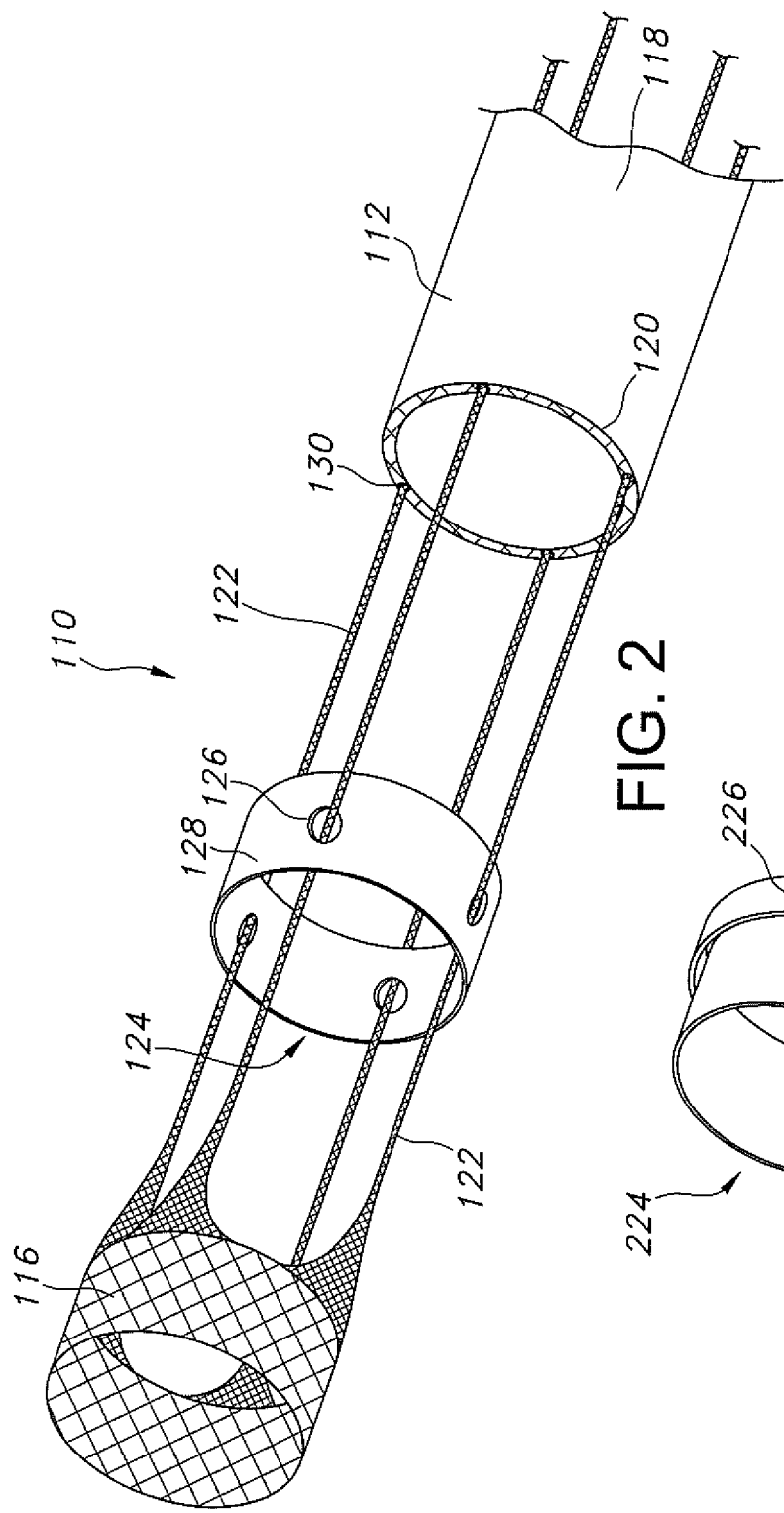
FIG. 2 illustrates a perspective view of an alternative embodiment of a steerable medical device according to the present invention.

Turning then to FIG. 2 there is illustrated a second embodiment of a steerable medical device, in particular a steerable catheter, generally indicated as 110. In this second embodiment like components have been accorded a like reference numeral and unless otherwise stated perform a like function.

FIG. 2 shows an exploded perspective view of the catheter 110, which comprises a main shaft 112 which is hollow and defines a main lumen 114 extending longitudinally there along, the main shaft 112 having a proximal end 118 and an opposed distal end 120. As with the first embodiment, the catheter 110 may be of any suitable size and formed from any suitable material or combination of materials. The main shaft 112 additionally incorporates a number of longitudinally extending auxiliary lumens 130 provided in the sidewall of the main shaft 112. Located in abutting engagement with the distal end 120 of the main shaft 112 is a retaining ring or pull ring 124 which includes a number of openings 126 in a sidewall 128 thereof. It will be appreciated as FIG. 2 illustrates an exploded view the pull ring 124 is shown longitudinally spaced from the distal end, but in use will be located directly in contact with the distal end 120.

The catheter 110 additionally comprises a braided sheath 116 which, while illustrated in spaced relationship to the pull ring 124 for the purposes of the exploded view shown, in use is located or formed on the exterior of the sidewall 128 of the pull ring 124, and again may be of any suitable configuration, for example comprising a forty eight end braid which splits into one or more braided actuators 122 each of which passes through one of the openings 126 before passing downwardly through the respective auxiliary lumen 130 and along the full length of the main shaft 112 before terminating at a handle (not shown) of the catheter 110, where again a suitable tensioning mechanism (not shown) is provided which is operable to selectively apply tension to one or more of the braided actuators 122 in order to again effect steering or displacement of the distal end 120. By forming or providing the braided sheath 116 around the pull ring 124, each of the braided actuators which extend from the braided sheath 116 are therefore secured or coupled to the pull ring 124 and thus effectively coupled to the distal end 20, again without requiring welding or the like.

Figure 3:
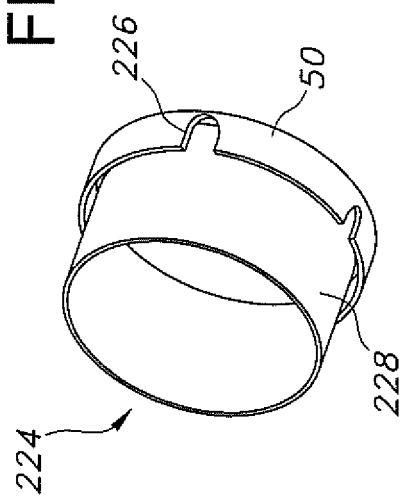
FIG. 3 illustrates an alternative pull-ring for use with the medical device illustrated in FIG. 2.

FIG. 3 illustrates an alternative pull ring 224 which may be utilised with the steerable catheter 110 illustrated in FIG. 2. The pull ring 224 includes a side wall 228 about which is provided a circumferential lip 50 at one end of the pull ring 224 which in use sits against the distal end 120 of the main shaft 112. A number of openings or grooves 226 are formed in the lip 50, which correspond in number and position to the number and position of the braided actuators 122. The braided sheath 116 would therefore again be provided about the exterior surface of the sidewall 228 and each of the braided actuators 122 passes through one of the grooves 226 before passing downwardly through the respective auxiliary lumen 130. This arrangement again avoids any requirement for welding, bonding or otherwise adhering the individual braided actuators 122 to the pull ring 226 or the distal end 120 of the main shaft 112.

Figure 4:
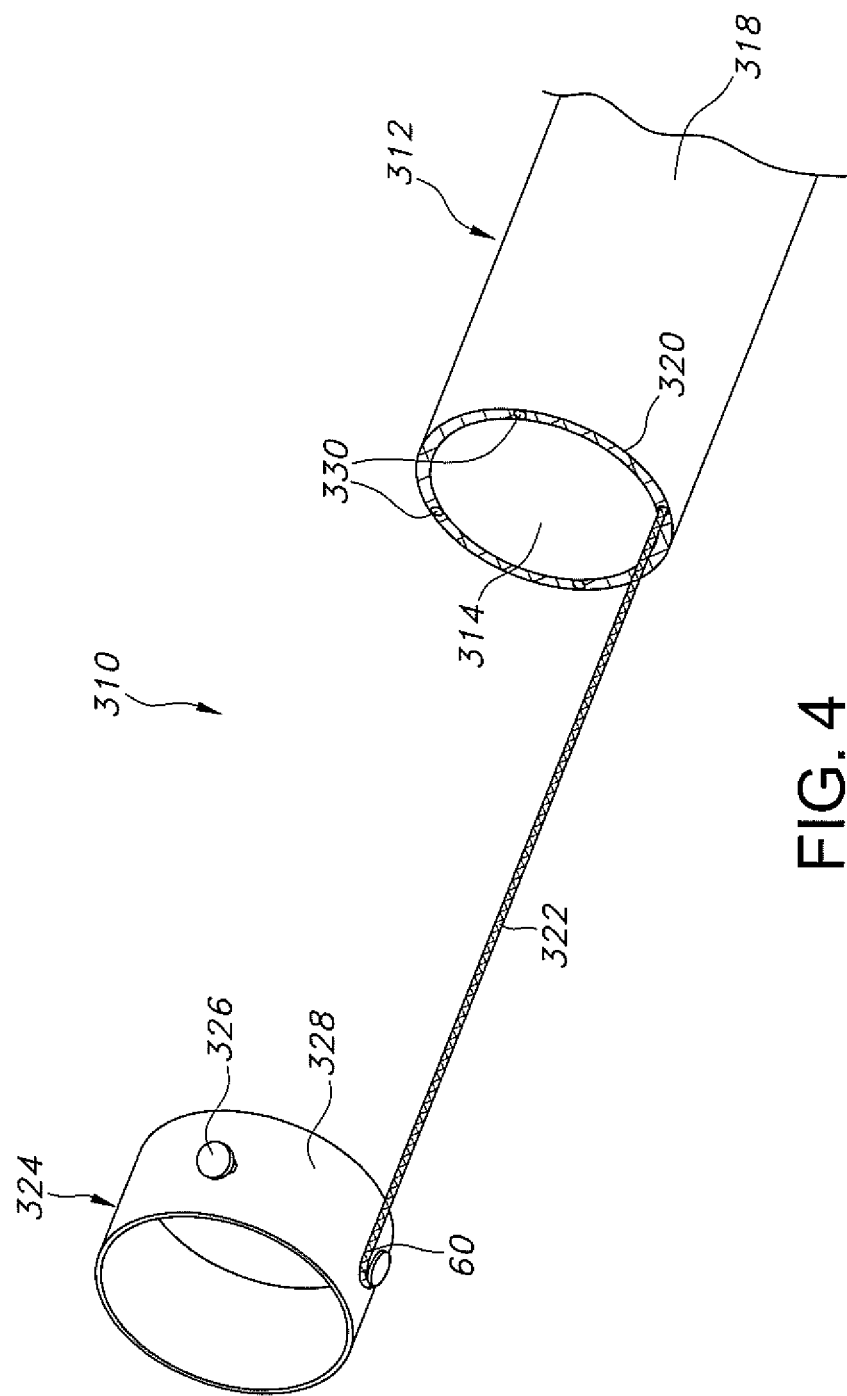
FIG. 4 illustrates a further alternative embodiment of a steerable medical device according to the present invention.

Turning now to FIG. 4 a further alternative embodiment of a steerable medical device according to the present invention is illustrated, generally indicated as 310. In this further alternative embodiment like components have been accorded like reference numerals and unless otherwise stated perform a like function.

The steerable catheter 310 comprises a hollow main shaft 312 defined in a main lumen 314 and an array of auxiliary lumens 330, in this case four circumferentially equally spaced auxiliary lumens 330. The main shaft 312 comprises a proximal end 318 and a distal end 320. Located adjacent to or in direct engagement with the distal end 320 is a pull ring 324 comprising a side wall 328 on which are provided a plurality of anchor points and, in the embodiment illustrated, four circumferentially equally spaced anchor points in the form of abutments 326.

The catheter 310 further comprises four braided actuators 322, although for illustrative purposes only one of the braided actuators 322 is shown. The braided actuators 322 are each provided with an integrated loop 60 at a free end thereof, which is formed from the individual braids constituting the braided actuator 322. The integrated loop 60 is shaped and dimensioned to be secured about the respective abutment 326 in order to couple the braided actuator 322 to the pull ring 324. It is also envisaged that the integrated loop 60 could be suitably enlarged in order to be dimensioned to loop directly around the distal end 320 which could then avoid the need for the pull ring 324.

Each of the braided actuators 322 then passes through the respective auxiliary lumen 330 to extend down the full length of the main shaft 312 to terminate at a handle (not shown) of the catheter 310, where each of the braided actuators 322 is suitably secured to a tensioning mechanism (not shown) operable to apply tension to the individual braided actuators 322 in order to steer the distal end 320 of the catheter 310. Each braided actuator 322 may for example include a second integrated loop (not shown) formed at the end of the braided actuator 322 located at the handle (not shown) thereby allowing the braided actuators 322 to be suitably secured to the handle or tensioning mechanism (not shown). This again avoids the requirement for welding or otherwise bonding the individual actuators 322.

In any of the catheters 10, 110, 310 the braid or braided actuators may be formed from a multifilament or monofilament yarn, or a combination thereof. In the case of a multifilament yarn the denier range is preferably between 5 denier and 500 denier. The multifilament yarn may be twisted, having either an S twist or a Z twist as is known in the art. The multifilament yarn may be ring spun or formed by any other suitable process, and may also be textured. For monofilament yarn the diameter can range between 0.025 mm and 3.0 mm.

The material or combination of materials chosen for the yarn(s) may be selected from one or more of the following: Liquid Crystal Polymer (LCP), Polytetrafluoroethylene (PTFE), Fluorinated ethylene propylene (FEP) Perfluoroalkoxy (PFA), Polyether ether ketone (PEEK), Polyvinylidene fluoride (PVDF), Polypropylene (PP), Polyester (PET), Nylon, Rayon, Polyamide, Ultra High Molecular Weigh Polyethylene (UHMWPE), Carbon, Glass Fibre, Cotton, Silk Viscose, Collagen, Calcium Alginate, Bio-absorbable Polyglycolic acid (PGA), 100% PGA, Polyglycolic acid-co-poly-L-lactic acid (PGA/PLLA), Poly-L-lactic acid (PLLA), 100% PLLA.

It will therefore be appreciated that the steerable catheters 10, 110, 310 of the present invention provide an alternative means of steering the distal end of the catheter and which may also utilise polymeric or non metallic materials in order to ensure that the catheter is MRI compatible in order to facilitate use during interventional procedures.

The invention claimed is:

1. A steerable medical device comprising:
   a) a main shaft having a main shaft length extending from a main shaft proximal end to a main shaft distal end;
   b) a pull ring secured at or adjacent to the distal end of the main shaft; and
   c) a braided sheath surrounding a proximal portion of the main shaft length, wherein at or adjacent to the main shaft distal end, the braided sheath splits into at least one braided actuator, and wherein the at least one braided actuator comprises an outward actuator leg extending towards and connected to the pull ring and a return actuator leg extending from the pull ring to the proximal end of the main shaft.

2. The steerable medical device of claim 1, wherein an outer sleeve encapsulates at least a portion of the braided sheath.

3. The steerable medical device of claim 1, wherein the at least one braided actuator is interwoven with the braided sheath.

4. The steerable medical device of claim 1, wherein at least one of the braided sheath and the at least one braided actuator is formed from a non-metallic material.

5. The steerable medical device of claim 1, wherein at least one of the braided sheath and the at least one braided actuator is formed from a polymeric material.

6. The steerable medical device of claim 1, wherein the pull ring comprises at least one anchor point to which the outward actuator leg of the at least one braided actuator is secured.

7. The steerable medical device of claim 1, wherein the pull ring has at least one fastener, and wherein the outward actuator leg of the at least on braided actuator has a closed loop that is connected to the at least one fastener.

8. The steerable medical device of claim 1, wherein the pull ring comprises an abutment, and wherein the outward actuator leg of the at least one braided actuator is connected to the abutment.

9. The steerable medical device of claim 1, wherein the main shaft comprises one or more lumens.

10. The steerable medical device of claim 1, wherein spaced proximally from the main shaft distal end, the braided sheath splits into at least two braided actuators, and wherein each of the at least two braided actuators comprises an outward actuator leg extending towards and connected to diametrically opposed locations on the pull ring and a return actuator leg extending from the pull ring to the proximal end of the main shaft.

11. The steerable medical device of claim 1, wherein spaced proximally from the main shaft distal end, the braided sheath splits into an array of braided actuators, and wherein each of the array of braided actuators comprises an outward actuator leg extending towards and connected to circumferentially equally spaced locations on the pull ring and a return actuator leg extending from the pull ring to the proximal end of the main shaft.

12. The steerable medical device of claim 1 in the form of a catheter.

13. The steerable medical device of claim 1, wherein the pull ring has a sidewall, and the braided sheath is located on an exterior surface of the pull ring sidewall.

14. The steerable medical device of claim 2, wherein the outer sleeve is at least partially affixed to the braided sheath.

15. The steerable medical device of claim 2, wherein the outer sleeve is characterized as having been at least partially reflowed over the braided sheath.

16. The steerable medical device of claim 6, wherein the at least one anchor point of the pull ring comprises an aperture through which the outward actuator leg of the at least one braided actuator passes.

17. The steerable medical device of claim 6, wherein the anchor point of the pull ring comprises at least one abutment to which the outward actuator leg of the at least one braided actuator is secured.

18. The steerable medical device of claim 6, wherein the anchor point of the pull ring comprises at least one groove to which the outward actuator leg of the at least one braided actuator is secured.

19. The steerable medical device of claim 9, wherein at least one of the one or more lumens defines a conduit that extends from the main shaft proximal end to the distal end of the main shaft, and wherein the return actuator leg of the at least one braided actuator extends through the conduit to the main shaft proximal end.

20. A steerable medical device comprising:
a) a main shaft having a main shaft length extending from a main shaft proximal end to a main shaft distal end, wherein the main shaft comprises two or more lumens and at least two of the lumens define two conduits that extend from the proximal end of the main shaft to the main shaft distal end;
b) a pull ring secured at or adjacent to the distal end of the main shaft; and
c) a braided sheath surrounding a proximal portion of the main shaft length, wherein spaced proximally from the main shaft distal end, the braided sheath splits into at least two braided actuators, and wherein each of the at least two braided actuators comprises an outward actuator leg extending towards and connected to diametrically opposed anchor locations on the pull ring and a return actuator leg that extends through one of the two conduits to the main shaft proximal end.

21. A steerable medical device comprising:
a) a main shaft having a main shaft length extending from a main shaft proximal end to a main shaft distal end, wherein the main shaft comprises at least four conduits that extend from the proximal end of the main shaft to the main shaft distal end;
b) a pull ring secured at or adjacent to the distal end of the main shaft; and
c) a braided sheath surrounding a proximal portion of the main shaft length, wherein at our adjacent to the main shaft distal end, the braided sheath splits into four braided actuators, and wherein each of the four braided actuators comprises an outward actuator leg extending towards and connected to circumferentially equally spaced anchor locations on the pull ring and a return actuator leg that extends through one of the four conduits to the main shaft proximal end.

* * * * *